United States Patent
Zheng

(10) Patent No.: US 9,538,781 B2
(45) Date of Patent: Jan. 10, 2017

(54) ORAL NICOTINE-SUBSTITUTED CYTISINE ATOMIZED LIQUID AND ITS PREPARATION METHOD

(71) Applicant: CHANGNING DEKANG BIOTECHNOLOGY CO., LTD, Shenzhen, Guangdong (CN)

(72) Inventor: Zhixuan Zheng, Guangdong (CN)

( * ) Notice: Subject to any disclaimer, the term of this patent is extended or adjusted under 35 U.S.C. 154(b) by 419 days.

(21) Appl. No.: 14/135,648

(22) Filed: Dec. 20, 2013

(65) Prior Publication Data
US 2014/0373855 A1 Dec. 25, 2014

Related U.S. Application Data

(63) Continuation of application No. PCT/CN2013/078913, filed on Jul. 5, 2013.

(30) Foreign Application Priority Data

Jun. 20, 2013 (CN) .......................... 2013 1 0256498

(51) Int. Cl.
*A24B 15/16* (2006.01)
*A61K 9/00* (2006.01)
*A61K 31/465* (2006.01)

(52) U.S. Cl.
CPC .............. *A24B 15/16* (2013.01); *A61K 9/007* (2013.01); *A61K 31/465* (2013.01)

(58) Field of Classification Search
USPC .............. 131/27 C, 369, 297–98, 29 C, 300, 309,131/310, 347, 352
See application file for complete search history.

(56) References Cited

U.S. PATENT DOCUMENTS

| | | | | |
|---|---|---|---|---|
| 3,316,919 A * | 5/1967 | Sydney | .................. | A24B 15/24 131/297 |
| 3,424,171 A * | 1/1969 | Rooker | .................. | A24B 15/24 131/297 |
| 4,131,117 A * | 12/1978 | Kite | .................. | A24B 15/24 131/297 |
| 4,986,286 A * | 1/1991 | Roberts | .................. | A24B 15/24 131/275 |
| 5,005,593 A * | 4/1991 | Fagg | .................. | A24B 15/24 131/297 |
| 5,074,319 A * | 12/1991 | White | .................. | A24B 15/26 131/298 |
| 5,099,862 A * | 3/1992 | White | .................. | A24B 15/24 131/297 |
| 5,243,999 A * | 9/1993 | Smith | .................. | A24B 15/24 131/290 |
| 5,301,694 A * | 4/1994 | Raymond | .................. | A24B 15/24 131/199 |
| 5,318,050 A * | 6/1994 | Gonzalez-Parra | .................. | A24B 15/12 131/290 |
| 5,435,325 A * | 7/1995 | Clapp | .................. | A24B 15/24 131/297 |
| 2006/0237024 A1 * | 10/2006 | Reich | .................. | A24B 3/12 131/270 |
| 2010/0031968 A1 * | 2/2010 | Sheikh | .................. | A24F 47/008 131/347 |
| 2010/0160376 A1 * | 6/2010 | Thompson | .................. | A23L 2/38 514/317 |
| 2010/0247586 A1 * | 9/2010 | Hugerth | .................. | A23G 1/32 424/401 |
| 2011/0162664 A1 * | 7/2011 | Liang | .................. | A24B 15/16 131/270 |
| 2012/0145170 A1 * | 6/2012 | O'Connell | .................. | A24B 15/24 131/298 |
| 2013/0008457 A1 * | 1/2013 | Zheng | .................. | A24B 15/24 131/297 |

FOREIGN PATENT DOCUMENTS

CN 101461566 B 1/2012
CN 101731750 B 8/2012

OTHER PUBLICATIONS

Product sheet for TWEEN® 80, Sigma-Aldrich, [online], retrieved from the Internet,[retrieved Jun. 27, 2014],<URL: http://www.sigmaaldrich.com/catalog/product/sigma/p4780?lang=en&region=US>.*

* cited by examiner

*Primary Examiner* — Dennis Cordray
(74) *Attorney, Agent, or Firm* — Prakash Nama; Global IP Services, PLLC

(57) ABSTRACT

The present patent application provides an oral nicotine-substituted cytisine atomized liquid and its preparation method. The oral nicotine-substituted cytisine atomized liquid includes the following components in mass percentage per 1 L of the oral atomized liquid: 0.1-10% of tobacco, 0.3-15% of cocoa extract, 0.1-0.9% of cytisine, 0.1-0.5% of TWEEN 80 and 75-90% of primer. The liquid can be obtained through the steps of weighing tobacco into an extraction tank, filtering the extract to obtain the filtrate, adding cocoa extract, cytisine and primer to the filtrate and mixing evenly.

3 Claims, No Drawings

ORAL NICOTINE-SUBSTITUTED CYTISINE ATOMIZED LIQUID AND ITS PREPARATION METHOD

CROSS-REFERENCE TO RELATED APPLICATIONS

This application is a Continuation Application of PCT Patent Application No. PCT/CN2013/078913 filed on Jul. 5, 2013, which claims the benefit of Chinese Patent Application No. 2013102564983 filed on Jun. 20, 2013; the contents of which is hereby incorporated by reference.

FIELD OF THE PATENT APPLICATION

The present patent application relates to an oral nicotine-substituted cytisine atomized liquid and its preparation method, under the technical field of chemical preparations.

BACKGROUND

Nicotine is an alkaloid present in the Solanaceae (nightshade) as well as an important component of tobacco. Nicotine is addictive or causes dependence, one of the most difficult drug addictions to get rid of that people find difficult to restrain from it. Repeated use of nicotine also increases heart rate and raises blood pressure and reduces appetite. Large dose of nicotine can cause vomiting and nausea, and even death in severe cases. Tobacco usually contains nicotine which makes smokers unable to quit smoking. However, current methods of smoking cessation generally employ nicotine-substitution method. Poor control still cannot reduce dependence on nicotine.

Clinical use of 0.15% cytisine aqueous solution for intramuscular or intravenous injections can treat reflex apnea induced by surgeries and various traumas, shock and neonatal asphyxia. Recent research reveals that this class of alkaloids also has many other pharmacological effects such as anti-arrhythmia, anti-microbial infection, anti-ulcer, elevation of white blood cell. In particular, the strong anti-cancer activity of these compounds can be used to produce smoking cessation medicine, emergency medicine and cough suppressants.

Cytisine has been sold across Eastern Europe under the trademark TABEX® as smoking cessation medicine since 1964. The use of cytisine in oral atomized liquids (electronic cigarette liquids) to substitute nicotine takes effect in getting rid of or not relying on nicotine. Current smoking cessation products, including electronic cigarettes, use nicotine to satisfy craving. However, nicotine is also extracted from tobacco and that the original meaning of smoking cessation is lost. Therefore, relapse of cigarette exists.

Oral nicotine-substituted cytisine atomized liquid, or known as electronic cigarette atomized liquid, is a popular alternative to cigarettes. Formulations and preparation process of electronic cigarette liquid, and its functions in healthcare have been reported in various literatures and patents. Chinese patent No. 200910310536.2 discloses an atomized liquid of an electronic simulated cigarette, a typical essence- and flavoring-formulated product, which comprises 25-90 parts of polyethylene glycol, 9-50 parts of propylene glycol and 0.3-52 parts of taste regulator. Chinese patent No. 200910104922.6 discloses an electronic cigarette atomized liquid, comprising 3-5% m/v of tobacco extract, 3-5% m/v of tobacco essence, 0-3% m/v of nicotine, 0.2-1% m/v of stabilizer, 3-8% m/v of thickening agent, 5-10% m/v of purified water, 50-70% m/v of propylene glycol, and optionally codeine phosphate, chlorpheniramine, or the like. Despite the use of tobacco extract, it is still a product formulated from tobacco extract and other essences and flavorings to imitate the taste of cigarettes. As more and more smokers adopt electronic cigarettes instead of cigarettes, some shortages of taking electronic cigarettes become more and more obvious. Smokers generally reflect that, although electronic cigarettes and cigarettes share similar shapes, textures and smoke, their aroma and taste are relatively different. In particular, they find difficult to adopt or get used to the aroma and taste of essence- and flavoring-formulated products. In addition, a common problem reflected by smokers is that aroma components of current electronic cigarette liquids are difficult to retain for a long time. The best ones can only be kept for about half a year, which "taste of cigarette" becomes very light or even gone. These shortages greatly affect the quality of electronic cigarette and restrict the prevalence and popularity of electronic cigarette.

SUMMARY

The objectives of the present patent application are to provide an oral nicotine-substituted cytisine atomized liquid and its preparation method, to enhance the aroma of electronic cigarette liquid, to improve the taste of electronic cigarette liquid and to reduce dependence on nicotine.

According to one aspect of the patent application, there is provided an oral nicotine-substituted cytisine atomized liquid, which include the following components in mass percentage per 1 L of the oral atomized liquid: 0.1-10% of tobacco, 0.3-15% of cocoa extract, 0.1-0.9% of cytisine, 0.1-0.5% of TWEEN 80 and 75-90% of primer.

In one embodiment, the primer may be propylene glycol, polyethylene glycol, glycerol or mixtures thereof.

According to another aspect of the patent application, there is provided a method of preparing oral nicotine-substituted cytisine atomized liquid, which may include the following steps:

(1) weighing the above mentioned mass/volume ratio of tobacco based on the target volume into an extraction tank with interlayer;

(2) measuring the above mentioned mass ratio of TWEEN 80 and 60-80% mass/volume ratio of primer based on the target volume respectively, adding TWEEN 80 into the primer, stir and mix for 20-40 minutes, adding the mixture into the extraction tank and soaking with tobacco for 30-90 minutes, then heating up to 40-60° C. by passing steam through the interlayer, extracting with heat preservation for 3-6 hours, releasing the extract and filtering to obtain the filtrate;

(3) adding the above mentioned mass percentage of cocoa extract to the filtrate, stirring and mixing for 30-60 minutes;

(4) adding the above mentioned mass percentage of cytisine into the filtrate; and (5) adding primer to the filtrate up to 100% of the target volume, stir and mix for 20-40 minutes and obtain the product after evenly mixed.

In one embodiment, the primer and TWEEN 80 may be both of pharmaceutical or food grades.

In one embodiment, the cocoa extract may be obtained by grinding cocoa beans into powder of 20-60 mesh, putting it into an extraction tank with interlayer, adding distilled water in an amount 3-10 times the weight of the cocoa bean powder, soaking the cocoa bean powder for 30-90 minutes, heating to 80-90° C., extracting with heat preservation for 2-6 hours, releasing and filtering the extract, and concentrating the filtrate under reduced pressure to give an extractive with specific gravity of 1.1-1.4.

The advantages of the present patent application are: addition of natural aroma component from plants into the oral nicotine-substituted cytisine atomized liquid provides an aroma closer to cigarette, better meets consumers' feeling about smoking, retains the natural aroma in the oral nicotine-substituted cytisine atomized liquid for a long time, enhances the aroma of electronic cigarette liquid, improves the taste of electronic cigarette liquid and reduces dependence on nicotine.

DETAILED DESCRIPTION

It should be understood that combinations of embodiments below only further illustrate the technical features of the present patent application and do not limit the scope of protection.

Example 1

1 L of oral nicotine-substituted cytisine atomized liquid includes the following components in mass percentage: 10% of tobacco, 3.6% of cocoa extract, 0.4% of cytisine, 0.2% of TWEEN 80 and 85.8% of primer.

The primer is a mixture of propylene glycol and glycerol in a ratio of 1:3.

A method of preparing the oral nicotine-substituted cytisine atomized liquid includes the following steps:
(1) with a target volume of 500 L, weighing the above mentioned mass/volume ratio of tobacco based on the target volume into an extraction tank with interlayer;
(2) measuring the above mentioned mass ratio of TWEEN 80 and 70% mass/volume ratio of primer based on the target volume respectively, add TWEEN 80 into the primer, stirring and mixing for 30 minutes, adding the mixture into the extraction tank and soaking with tobacco for 50 minutes, then heating up to 50° C. by passing steam through the interlayer, extracting with heat preservation for 4 hours, releasing the extract and filtering to obtain the filtrate;
(3) adding the above mentioned mass percentage of cocoa extract to the filtrate, stirring and mixing for 40 minutes;
(4) adding the above mentioned mass percentage of cytisine into the filtrate; and
(5) adding primer to the filtrate up to 100% of the target volume, stirring and mixing for 30 minutes and obtaining the product after evenly mixed.

The cocoa extract is obtained by grinding cocoa beans into powder of 60 mesh, putting it into an extraction tank with interlayer, adding distilled water in an amount 10 times the weight of the cocoa bean powder, soaking the cocoa bean powder for 90 minutes, heating to 90° C., extracting with heat preservation for 6 hours, releasing and filtering the extract, and concentrating the filtrate under reduced pressure to give an extractive with specific gravity of 1.1.

Example 2

An oral nicotine-substituted cytisine atomized liquid includes the following components in mass percentage per 1 L of the oral atomized liquid: 10% of tobacco, 4% of cocoa extract, 0.3% of cytisine, 0.3% of TWEEN 80 and 85.4% of primer.

The primer is a mixture of propylene glycol and polyethylene glycol in a ratio of 1:2.

A method of preparing an oral nicotine-substituted cytisine atomized liquid includes the following steps:
(1) with a target volume of 500 L, weighing the above mentioned mass/volume ratio of tobacco based on the target volume into an extraction tank with interlayer;
(2) measuring the above mentioned mass ratio of TWEEN 80 and 76% mass/volume ratio of primer based on the target volume respectively, adding TWEEN 80 into the primer, stirring and mixing for 30 minutes, adding the mixture into the extraction tank and soaking with tobacco for 60 minutes, then heating up to 60° C. by passing steam through the interlayer, extracting with heat preservation for 6 hours, releasing the extract and filtering to obtain the filtrate;
(3) adding the above mentioned mass percentage of cocoa extract to the filtrate, stirring and mixing for 40 minutes;
(4) adding the above mentioned mass percentage of cytisine into the filtrate; and
(5) adding primer to the filtrate up to 100% of the target volume, stirring and mixing for 30 minutes and obtaining the product after evenly mixed.

The cocoa extract is obtained by grinding cocoa beans into powder of 20 mesh, putting it into an extraction tank with interlayer, adding distilled water in an amount 3 times the weight of the cocoa bean powder, soaking the cocoa bean powder for 30 minutes, heating to 80° C., extracting with heat preservation for 2 hours, releasing and filtering the extract, and concentrating the filtrate under reduced pressure to give an extractive with specific gravity of 1.4.

Example 3

An oral nicotine-substituted cytisine atomized liquid includes the following components in mass percentage per 1 L of the oral atomized liquid: 0.1% of tobacco, 10% of cocoa extract, 0.9% of cytisine, 0.5% of TWEEN 80 and 88.5% of primer.

The primer is a mixture of polyethylene glycol and glycerol in a ratio of 1:5.

A method of preparing an oral nicotine-substituted cytisine atomized liquid includes the following steps:
(1) with a target volume of 300 L, weighing the above mentioned mass/volume ratio of tobacco based on the target volume into an extraction tank with interlayer;
(2) measuring the above mentioned mass ratio of TWEEN 80 and 80% mass/volume ratio of primer based on the target volume respectively, adding TWEEN 80 into the primer, stirring and mixing for 20 minutes, adding the mixture into the extraction tank and soaking with tobacco for 30 minutes, then heating up to 55° C. by passing steam through the interlayer, extracting with heat preservation for 3 hours, releasing the extract and filtering to obtain the filtrate;
(3) adding the above mentioned mass percentage of cocoa extract to the filtrate, stirring and mixing for 30 minutes;
(4) adding the above mentioned mass percentage of cytisine into the filtrate; and
(5) adding primer to the filtrate up to 100% of the target volume, stirring and mixing for 20 minutes and obtain the product after evenly mixed.

The cocoa extract is obtained by grinding cocoa beans into powder of 40 mesh, putting it into an extraction tank with interlayer, adding distilled water in an amount 5 times the weight of the cocoa bean powder, soaking the cocoa bean powder for 50 minutes, heating to 85° C., extracting with heat preservation for 3 hours, releasing and filtering the extract, and concentrating the filtrate under reduced pressure to give an extractive with specific gravity of 1.2.

Example 4

An oral nicotine-substituted cytisine atomized liquid includes the following components in mass percentage per 1 L of the oral atomized liquid: 5% of tobacco, 15% of cocoa extract, 0.1% of cytisine, 0.1% of TWEEN 80 and 79.8% of primer.

The primer is polyethylene glycol.

A method of preparing an oral nicotine-substituted cytisine atomized liquid includes the following steps:
(1) with a target volume of 400 L, weighing the above mentioned mass/volume ratio of tobacco based on the target volume into an extraction tank with interlayer;
(2) measuring the above mentioned mass ratio of TWEEN 80 and 60% mass/volume ratio of primer based on the target volume respectively, adding TWEEN 80 into the primer, stirring and mixing for 40 minutes, adding the mixture into the extraction tank and soaking with tobacco for 90 minutes, then heating up to 40° C. by passing steam through the interlayer, extracting with heat preservation for 6 hours, releasing the extract and filtering to obtain the filtrate;
(3) adding the above mentioned mass percentage of cocoa extract to the filtrate, stirring and mixing for 60 minutes;
(4) adding the above mentioned mass percentage of cytisine into the filtrate; and
(5) adding primer to the filtrate up to 100% of the target volume, stirring and mixing for 40 minutes and obtaining the product after evenly mixed.

The cocoa extract is obtained by grinding cocoa beans into powder of 50 mesh, putting it into an extraction tank with interlayer, adding distilled water in an amount 8 times the weight of the cocoa bean powder, soaking the cocoa bean powder for 60 minutes, heating to 90° C., extracting with heat preservation for 5 hours, releasing and filtering the extract, and concentrating the filtrate under reduced pressure to give an extractive with specific gravity of 1.4.

Example 5

An oral nicotine-substituted cytisine atomized liquid includes the following components in mass percentage per 1 L of the oral atomized liquid: 8.6% of tobacco, 0.3% of cocoa extract, 0.7% of cytisine, 0.4% of TWEEN 80 and 90% of primer.

The primer is glycerol.

A method of preparing an oral nicotine-substituted cytisine atomized liquid includes the following steps:
(1) with a target volume of 500 L, weighing the above mentioned mass/volume ratio of tobacco based on the target volume into an extraction tank with interlayer;
(2) measuring the above mentioned mass ratio of TWEEN 80 and 65% mass/volume ratio of primer based on the target volume respectively, adding TWEEN 80 into the primer, stirring and mixing for 35 minutes, adding the mixture into the extraction tank and soaking with tobacco for 40 minutes, then heating up to 45° C. by passing steam through the interlayer, extracting with heat preservation for 5 hours, releasing the extract and filtering to obtain the filtrate;
(3) adding the above mentioned mass percentage of cocoa extract to the filtrate, stirring and mixing for 45 minutes;
(4) adding the above mentioned mass percentage of cytisine into the filtrate; and
(5) adding primer to the filtrate up to 100% of the target volume, stirring and mixing for 30 minutes and obtaining the product after evenly mixed.

The cocoa extract is obtained by grinding cocoa beans into powder of 40 mesh, putting it into an extraction tank with interlayer, adding distilled water in an amount 7 times the weight of the cocoa bean powder, soaking the cocoa bean powder for 80 minutes, heating to 90° C., extracting with heat preservation for 5 hours, releasing and filtering the extract, and concentrating the filtrate under reduced pressure to give an extractive with specific gravity of 1.3.

Example 6

An oral nicotine-substituted cytisine atomized liquid includes the following components in mass percentage per 1 L of the oral atomized liquid: 10% of tobacco, 14% of cocoa extract, 0.7% of cytisine, 0.3% of TWEEN 80 and 75% of primer.

The primer is a mixture of propylene glycol, polyethylene glycol and glycerol in a ratio of 1:1:3.

A method of preparing an oral nicotine-substituted cytisine atomized liquid includes the following steps:
(1) with a target volume of 400 L, weighing the above mentioned mass/volume ratio of tobacco based on the target volume into an extraction tank with interlayer;
(2) measuring the above mentioned mass ratio of TWEEN 80 and 75% mass/volume ratio of primer based on the target volume respectively, adding TWEEN 80 into the primer, stirring and mixing for 35 minutes, adding the mixture into the extraction tank and soaking with tobacco for 60 minutes, then heating up to 50° C. by passing steam through the interlayer, extracting with heat preservation for 4 hours, releasing the extract and filtering to obtain the filtrate;
(3) adding the above mentioned mass percentage of cocoa extract to the filtrate, stirring and mixing for 40 minutes;
(4) adding the above mentioned mass percentage of cytisine into the filtrate; and
(5) adding primer to the filtrate up to 100% of the target volume, stirring and mixing for 30 minutes and obtain the product after evenly mixed.

The cocoa extract is obtained by grinding cocoa beans into powder of 60 mesh, putting it into an extraction tank with interlayer, adding distilled water in an amount 10 times the weight of the cocoa bean powder, soaking the cocoa bean powder for 90 minutes, heating to 90° C., extracting with heat preservation for 6 hours, releasing and filtering the extract, and concentrating the filtrate under reduced pressure to give an extractive with specific gravity of 1.1.

What is claimed is:

1. A method of preparing oral nicotine-substituted cytisine atomized liquid comprising the following components in mass percentage per 1 L of the oral nicotine-substituted cytisine atomized liquid: 0.1-10% of tobacco, 0.3-15% of cocoa extract, 0.1-0.9% of cytisine, 0.1-0.5% of Polysorbate 80 and 75-90% of primer, wherein the primer is propylene glycol, polyethylene glycol, glycerol or mixtures thereof; the method comprises the following steps:
(1) weighing the tobacco according to said mass percentage; putting the tobacco into an extraction tank;
(2) measuring the Polysorbate 80 according to said mass percentage and the primer according to said mass percentage respectively, adding the Polysorbate 80 into the primer, stirring and mixing the Polysorbate 80 and the primer for 20-40 minutes to obtain a mixture, adding the mixture into the extraction tank and soaking the tobacco with the mixture for 30-90 minutes, then heating up the tobacco to a temperature of 40-60° C. by introducing steam in the extraction tank, extracting the tobacco for 3-6 hours to obtain an extract while maintaining the temperature during extraction, filtering the extract to obtain a filtrate;

(3) stirring and mixing the cocoa extract according to said mass percentage with the filtrate for 30-60 minutes;

(4) adding the cytisine according to said mass percentage into the filtrate; and (5) adding the primer according to said mass percentage to the filtrate to reach an intended total volume of the oral nicotine-substituted cytisine atomized liquid, stirring and mixing the filtrate for 20-40 minutes until the filtrate is evenly mixed, thereby obtaining the oral nicotine-substituted cytisine atomized liquid.

2. The method of preparing oral nicotine-substituted cytisine atomized liquid according to claim 1, wherein the primer and the Polysorbate 80 are both of pharmaceutical or food grades.

3. The method of preparing oral nicotine-substituted cytisine atomized liquid according to claim 1, wherein the cocoa extract is obtained by the following steps:

grinding cocoa beans into powder of 20-60 mesh, putting the powder into a second extraction tank, adding distilled water to the powder in an amount 3-10 times the weight of the powder, soaking the powder with the distilled water for 30-90 minutes, heating the soaked powder to a temperature of 80-90° C., extracting the powder for 2-6 hours to obtain an extract while maintaining the temperature during extraction, filtering the extract to obtain a filtrate, and concentrating the filtrate to obtain the cocoa extract with specific gravity of 1.1-1.4.

* * * * *